United States Patent [19]

Seko et al.

[11] Patent Number: 5,648,496

[45] Date of Patent: Jul. 15, 1997

[54] PROCESS FOR PRODUCING AMINONITROPYRIDINES

[75] Inventors: Shinzo Seko; Kunihito Miyake, both of Osaka, Japan

[73] Assignee: Sumitomo Chemical Company, Limited, Osaka, Japan

[21] Appl. No.: 623,039

[22] Filed: Mar. 28, 1996

[30] Foreign Application Priority Data

Mar. 28, 1995 [JP] Japan .................. 7-069203
Dec. 4, 1995 [JP] Japan .................. 7-315234

[51] Int. Cl.$^6$ .................. C07D 213/73; C07D 213/84
[52] U.S. Cl. .................. 546/307; 546/286; 546/287
[58] Field of Search .................. 546/286, 287, 546/307

[56] References Cited

U.S. PATENT DOCUMENTS

| | | | |
|---|---|---|---|
| 4,552,967 | 11/1985 | Greene et al. | 546/307 |
| 4,567,272 | 1/1986 | Orth et al. | 546/307 |
| 5,262,539 | 11/1993 | Makosza et al. | 546/307 |
| 5,498,715 | 3/1996 | Kuo et al. | 546/318 |

FOREIGN PATENT DOCUMENTS

| | | |
|---|---|---|
| 0 453 885 A2 | 10/1991 | European Pat. Off. . |
| 7-109260 | 4/1996 | Japan . |

OTHER PUBLICATIONS

Marian Wozniak et al., Regioselectivity of the Amination . . . , Liebigs Ann. Chem., 875, 1991.
Boyer et al., 2, 3-T-Dinitrosopyridines, J. Am. Chem. Soc. 78, 423, 1956.

*Primary Examiner*—Zinna Northington Davis

[57] ABSTRACT

A process for producing an aminonitropyridine represented by the general formula [1], which comprises reacting a nitropyridine represented by the general formula [2] (wherein $X^1$, $X^2$ and $X^3$ indicate a hydrogen atom, a halogen atom, a nitro group, a cyano group, an aryl group, an aromatic heterocycle or an alkyl group, etc.; Y is an oxygen atom; and n is 0 or 1) with an O-substituted hydroxylamine represented by the general formula [3] (wherein $R^4$ is a hydrogen atom, an alkyl group, a cycloalkyl group or an aralkyl group; and $R^5$ is an alkyl group or an aralkyl group) or a salt thereof in the presence of a base and a metal catalyst.

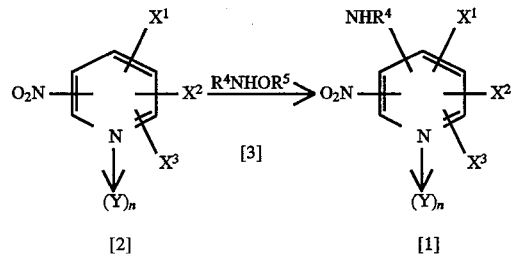

15 Claims, No Drawings

PROCESS FOR PRODUCING AMINONITROPYRIDINES

BACKGROUND OF THE INVENTION

1. Field of the Invention

The present invention relates to a process for producing an aminonitropyridine by a direct amination reaction of a nitropyridine using an O-substituted hydroxylamine or a salt thereof.

2. Description of the Related Art

An aminonitropyridine can be a precursor of a diaminopyridine and is an important compound as an intermediate of drugs and agricultural chemicals. As the process for synthesizing an aminonitropyridine from a nitropyridine, there has generally been known a process via a substitution reaction between a halogenated nitropyridine and an amine. However, such a process has the disadvantages of having a large number of steps and the requirement of a halogenation step causing high corrosion and a large environmental load.

Some attempts to directly produce an aminonitropyridine from a nitropyridine have been made. However, for example, a process of direct amination of a nitropyridine using a hydroxylamine hydrochloride salt (J. Am. Chem. Soc. 78, 423 (1956)) is not satisfactory because of the reaction yield. In addition, a process of directly aminating a nitropyridine using ammonia and potassium permanganate (Liebigs Ann. Chem. 875 (1991)) has the drawback that a complicated operation is required because one or more equivalents of explosive potassium permanganate is used. A process using 1-sulphenamoylthiocarbonylpyrrolidine as an amination agent (Japanese Laid-Open Patent Publication No. 7-109260) is inferior in industrial utility because the amination agent is expensive.

SUMMARY OF THE INVENTION

It is an object of the present invention to provide a process which is industrially advantageous for producing an aminonitropyridine.

The present inventors have made extensive studies in order to develop a process for producing an aminonitropyridine in an industrially advantageous manner. As a result, it has been found that an aminonitropyridine can be obtained in one step by directly aminating a nitropyridine with an O-substituted hydroxylamine in the presence of a base and a metal catalyst. Thus, the present invention has been accomplished.

The present invention provides a process for producing an aminonitropyridine represented by the general formula [1]:

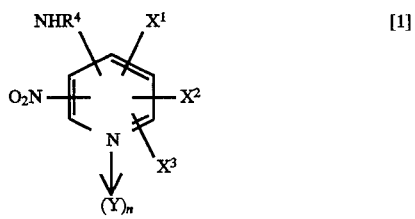

wherein $X^1$, $X^2$, $X^3$, $R^4$, Y and n are as defined below, which comprises reacting a nitropyridine represented by the general formula [2]:

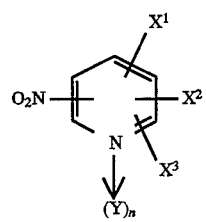

wherein $X^1$, $X^2$ and $X^3$ are the same or different and indicate a hydrogen atom, a halogen atom, a nitro group, a cyano group, an aryl group, a heterocycle, an alkyl group, a cycloalkyl group, an alkenyl group (the alkyl group, the cycloalkyl group and the alkenyl group may be respectively substituted with a halogen atom, an aryl group, an amino group, a hydroxyl group, a carboxyl group or an alkoxyl group), or a group $OR^1$, $SR^1$, $NR^1R^2$, $COR^3$, $COOR^3$, $CONR^1R^2$, $SO_2R^3$, $SO_3R^3$ or $SO_2NR^1R^2$, or when two of $X^1$, $X^2$ and $X^3$ bond at the ortho-position, the two may bond together so that a 5- to 7-membered hydrocarbon ring or heterocycle is formed which includes 2 carbon atoms of the pyridine ring; $R^1$ and $R^2$ are the same or different and indicate a hydrogen atom, an alkyl group, an alkenyl group (the alkyl group and the alkenyl group may be respectively substituted with a halogen atom, an aryl group, an amino group, a hydroxyl group, a carboxyl group or an alkoxyl group), an aryl group or an acyl group; $R^3$ is a hydrogen atom, an alkyl group, an alkenyl group (the alkyl group and the alkenyl group may be respectively substituted with a halogen atom, an aryl group, an amino group, a hydroxyl group, a carboxyl group or an alkoxyl group) or an aryl group; Y is an oxygen atom; and n is 0 or 1, with an O-substituted hydroxylamine represented by the general formula [3]:

$$R^4NHOR^5 \qquad [3]$$

wherein $R^4$ is a hydrogen atom, an alkyl group, a cycloalkyl group or an aralkyl group; and $R^5$ is an alkyl group or an aralkyl group, or a salt thereof in the presence of a base and a metal catalyst.

DETAILED DESCRIPTION OF THE INVENTION

In the nitropyridine represented by general formula [2], the O-substituted hydroxylamine represented by general formula [3] and the aminonitropyridine represented by general formula [1], which are used in the present invention, the alkyl group indicates a straight-chain or branched alkyl group having 1 to 6 carbon atoms, and examples thereof include methyl group, ethyl group, n-propyl group, n-butyl group, n-pentyl group, isopropyl group, sec-butyl group, tert-butyl group, neopentyl group, etc.

The alkoxy group indicates a straight-chain or branched alkoxyl group having 1 to 6 carbon atoms, and examples thereof include methoxy group, ethoxy group, n-propoxy group, n-butoxy group, n-pentoxy group, isopropoxy group, sec-butoxy group, tert-butoxy group, neopentoxy group, etc.

The aryl group indicates a monocyclic or polycyclic aromatic hydrocarbon ring having 6 to 14 carbon atoms. The heterocycle indicates a monocyclic or polycyclic, and aromatic or 3- to 6-membered non-aromatic heterocycle. Examples thereof include phenyl group, naphthyl group, anthryl group, furyl group, pyrrolyl group, thienyl group, oxazolyl group, thiazolyl group, pyridyl group, imidazolyl group, triazolyl group, tetrazolyl group, quinolyl group, oxirane ring, aziridine ring, dihydrofuran ring, tetrahydrofuran ring, dihydropyran ring, tetrahydropyran ring, 1,3-dioxorane ring, pyrrolidine ring, piperidine ring, morpholine ring etc., each of which may have various substituents.

The cycloalkyl group indicates a cycloalkyl having 3 to 6 carbon atoms, and examples thereof include cyclopropyl group, cyclopentyl group, cyclohexyl group etc.

The alkenyl group indicates a straight-chain or branched unsaturated hydrocarbon group having 2 to 6 carbon atoms and a carbon-carbon double bond, and examples thereof include vinyl group, allyl group, propenyl group, butenyl group, pentenyl group, etc.

Examples of the aralkyl group include benzyl group, etc. Examples of the acyl group include acetyl group, propionyl group, butyryl group, isobutyryl group, valeryl group, isovaleryl group, pivaloyl group, hexanoyl group, benzoyl group, etc.

Examples of the nitropyridine represented by the general formula [2] include 2-nitropyridine, 3-halogeno-2-nitropyridine, 3-cyano-2-nitropyridine, 3-aryl-2-nitropyridine, 3-alkyl-2-nitropyridine, 3-alkenyl-2-nitropyridine, 3-hydroxy-2-nitropyridine, 3-alkoxy-2-nitropyridine, 3-alkenyloxy-2-nitro-pyridine, 3-aryloxy-2-nitropyridine, 3-benzyloxy-2-nitropyridine, 3-acyloxy-2-nitropyridine, 3-amino-2-nitropyridine, 3-(N-alkylamino)-2-nitropyridine, 3-(N-alkenylamino)-2-nitropyridine, 3-(N-arylamino)-2-nitropyridine, 3-(N-acylamino)-2-nitropyridine, 3-(N,N-dialkylamino)-2-nitropyridine, 3-acetyl-2-nitropyridine, 3-alkenylcarbonyl-2-nitropyridine, 3-arylcarbonyl-2-nitropyridine, 3-benzylcarbonyl-2-nitropyridine, 3-alkoxycarbonyl-2-nitropyridine, 3-alkenyloxycarbonyl-2-nitropyridine, 2,3-dinitropyridine, 3-benzyl-2-nitropyridine, 2-nitro-3-pyridinecarboxylic acid, 3-aryloxy-carbonyl-2-nitropyridine, 3-benzyloxycarbonyl-2-nitropyridine, 3-mercapto-2-nitropyridine, 3-alkylthio-2-nitropyridine, 3-alkenylthio-2-nitropyridine, 3-arylthio-2-nitropyridine, 3-benzylthio-2-nitropyridine, 3-acylthio-2-nitropyridine, 2-nitro-3-pyridinesulfonic acid, alkyl 2-nitro-3-pyridinesulfonate, alkenyl 2-nitro-3-pyridinesulfonate, aryl 2-nitro-3-pyridinesulfonate, benzyl 2-nitro-3-pyridinesulfonate, 3-trifluoromethyl-2-nitropyridine, 3-chloromethyl-2-nitropyridine, 3-(2-methoxyethyl)-2-nitropyridine, 3-trifluoromethoxy-2-nitropyridine, 3-difluoromethoxy-2-nitropyridine, 3-(2-methoxyethoxy)-2-nitropyridine, 3-(2-chlorovinyl)-2-nitropyridine, 3-(α-styryl)-2-nitropyridine, 3-(3-methoxy-1-propenyl)-2-nitropyridine, 3-cycloalkyl-2-nitropyridine, 3-fluorocyclopropyl-2-nitropyridine, 3-(2-oxazolinyl)-2-nitropyridine, 3-(4-piperidyl)-2-nitropyridine, 3-alkylsulfonyl-2-nitropyridine, 3-alkenylsulfonyl-2-nitropyridine, 3-arylsulfonyl-2-nitropyridine, 3-benzylsulfonyl-2-nitropyridine, 2-nitro-3-pyridinecarboxamide, N-alkyl-2-nitro-3-pyridinecarboxamide, N-alkenyl-2-nitro-3-pyridinecarboxamide, N-aryl-2-nitro-3-pyridinecarboxamide, N-acyl-2-nitro-3-pyridinecarboxamide, N,N-dialkyl-2-nitro-3-pyridinecarboxamide, 2-nitro-3-pyridinesulfonamide, N-alkyl-2-nitro-3-pyridinesulfonamide, N-alkenyl-2-nitro-3-pyridinesulfonamide, N-aryl-2-nitro-3-pyridinesulfonamide, N-acyl-2-nitro-3-pyridinesulfonamide, N,N-dialkyl-2-nitro-3-pyridinesulfonamide, 3-(N-benzylamino)-2-nitropyridine, N-benzyl-2-nitro-3- pyridinesulfonamide, N-benzyl-2-nitro-3-pyridinecarboxamide and isomers of the above 3-substituted-2-nitropyridines, isomers having a substituent on the 4-, 5- or 6-position instead of the 3-position, 3-nitropyridine, 2-halogeno-3-nitropyridine, 2-cyano-3-nitropyridine, 2-aryl-3-nitropyridine, 2-alkyl-3-nitropyridine, 2-alkenyl-3-nitropyridine, 2-hydroxy-3-nitropyridine, 2-alkoxy-3-nitropyridine, 2-alkenyloxy-3-nitro-pyridine, 2-aryloxy-3-nitropyridine, 2-benzyloxy-3-nitropyridine, 2-acyloxy-3-nitropyridine, 2-amino-3-nitropyridine, 2-(N-alkylamino)-3-nitropyridine, 2-(N-alkenylamino)-3-nitropyridine, 2-(N-arylamino)-3-nitropyridine, 2-(N-acylamino)-3-nitropyridine, 2-(N,N-dialkylamino)-3-nitropyridine, 2-acetyl-3-nitropyridine, 2-alkenylcarbonyl-3-nitropyridine, 2-arylcarbonyl-3-nitropyridine, 2-benzylcarbonyl-3-nitropyridine, 2-alkoxycarbonyl-3-nitropyridine, 2-alkenyloxycarbonyl-3-nitropyridine, 2-benzyl-3-nitropyridine, 3-nitro-2-pyridinecarboxylic acid, 2-aryloxycarbonyl-3-nitropyridine, 2-benzyloxycarbonyl-3-nitropyridine, 2-mercapto-3-nitropyridine, 2-alkylthio-3-nitropyridine, 2-alkenylthio-3-nitropyridine, 2-arylthio-3-nitropyridine, 2-benzylthio-3-nitropyridine, 2-acylthio-3-nitropyridine, 3-nitro-2-pyridinesulfonic acid, alkyl 3-nitro-2-pyridinesulfonate, alkenyl 3-nitro-2-pyridinesulfonate, aryl 3-nitro-2-pyridinesulfonate, benzyl 3-nitro-2-pyridinesulfonate, 2-trifluoromethyl-3-nitropyridine, 2-chloromethyl-3-nitropyridine, 2-(2-methoxyethyl)-3-nitropyridine, 2-trifluoromethoxy-3-nitropyridine, 2-difluoromethoxy-3-nitropyridine, 2-(2-methoxyethoxy)-3-nitropyridine, 2-(2-chlorovinyl)-3-nitropyridine, 2-(α-styryl)-3-nitropyridine, 2-(3-methoxy-1-propenyl)-3-nitropyridine, 2-cycloalkyl-3-nitropyridine, 2-fluorocyclopropyl-3,nitropyridine, 2-(2-oxazolinyl)-3-nitropyridine, 2-(4-piperidyl)-3-nitropyridine, 2-(alkylsulfonyl)-3-nitropyridine, 2-(alkenylsulfonyl)-3-nitropyridine, 2-(arylsulfonyl)-3-nitropyridine, 2-benzylsulfonyl)-3-nitropyridine, 3-nitro2-pyridinecarboxamide, N-alkyl-3-nitro-2-pyridinecarboxamide, N-alkenyl-3-nitro-2-pyridinecarboxamide, N-aryl-3-nitro-2-pyridinecarboxamide, N-acyl-3-nitro-2-pyridinecarboxamide, N,N-dialkyl-3-nitro-2-pyridinecarboxamide, 3-nitro-2-pyridinesulfonamide, N-alkyl-3-nitro-2-pyridinesulfonamide, N-alkenyl-3-nitro-2-pyridinesulfonamide, N-aryl-3-nitro-2-pyridinesulfonamide, N-acyl-3-nitro-2-pyridinesulfonamide, N,N-dialkyl-3-nitro-2-pyridinesulfonamide, 2-(N-benzylamino)-3-nitropyridine, N-benzyl-3-nitro-2- pyridinesulfonamide, N-benzyl-3-nitro-2-pyridinecarboxamide and isomers of the above 2-substituted-3-nitropyridines, isomers having a substituent on the 4-, 5- or 6-position instead of the 2-position, 4-nitropyridine, 3-halogeno-4-nitropyridine, 3-cyano-4-nitropyridine, 3-aryl-4-nitropyridine, 3-alkyl-4-nitropyridine, 3-alkenyl-4-nitropyridine, 3-hydroxy-4-nitropyridine, 3-alkoxy-4-nitropyridine, 3-alkenyloxy-4-nitro-pyridine, 3-aryloxy-4-nitropyridine, 3-benzyloxy-4-nitropyridine, 3-acyloxy-4-nitropyridine, 3-amino-4-nitropyridine, 3-(N-alkylamino)-4-nitropyridine, 3-(N-alkenylamino)-4-nitropyridine, 3-(N-arylamino)-4-nitropyridine, 3-(N-acylamino)-4-nitropyridine, 3-(N,N-dialkylamino)-4-nitropyridine, 3-acetyl-4-nitropyridine, 3-alkenylcarbonyl-4-nitropyridine, 3-arylcarbonyl-4-nitropyridine, 3-benzylcarbonyl-4-nitropyridine, 3-alkoxycarbonyl-4-nitropyridine, 3-alkenyloxycarbonyl-4-nitropyridine, 3,4-dinitropyridine, 3-benzyl-4-nitropyridine, 4-nitro-3-pyridinecarboxylic acid, 3-aryloxycarbonyl-4-nitropyridine, 3-benzyloxycarbonyl-4-nitropyridine, 3-mercapto-4-nitropyridine, 3-alkylthio-4-nitropyridine, 3-alkenylthio-4-nitropyridine, 3-arylthio-4-nitropyridine, 3-benzylthio-4-nitropyridine, 3-acylthio-4-nitropyridine, 4-nitro-3-pyridinesulfonic acid, alkyl 4-nitro-3- pyridinesulfonate, alkenyl 4-nitro-3-pyridinesulfonate, aryl 4-nitro-3-pyridinesulfonate, benzyl 4-nitro-3-pyridinesulfonate, 3-trifluoromethyl-4-nitropyridine, 3-chloromethyl-4-nitropyridine, 3-(2-methoxyethyl)-4-nitropyridine, 3-trifluoromethoxy-4-nitropyridine, 3-difluoromethoxy-4-nitropyridine, 3-(2-methoxyethoxy)-4-nitropyridine, 3-(2-chlorovinyl)-4-nitropyridine, 3-(α-styryl)-4-nitropyridine, 3-(3-methoxy-1-propenyl)-4-nitropyridine, 3-cycloalkyl-4-nitropyridine, 3-fluorocyclopropyl-4-nitropyridine, 3-(2-oxazolinyl)-4-nitropyridine, 3-(4-piperidyl)-4-nitropyridine, 3-alkylsulfonyl-4-nitropyridine, 3-alkenylsulfonyl-4-nitropyridine, 3-arylsulfonyl-4-nitropyridine, 3-benzylsulfonyl-4-nitropyridine, 4-nitro-3-pyridinecarboxamide, N-alkyl-4-nitro-3-pyridinecarboxamide, N-alkenyl-4-nitro-3-pyridinecarboxamide, N-aryl-4-nitro-3-pyridinecarboxamide, N-acyl-4-nitro-3-pyridinecarboxamide, N,N-dialkyl-4-nitro-3-pyridinecarboxamide, 4-nitro-3-pyridinesulfonamide, N-alkyl-4-nitro-3pyridinesulfonamide, N-alkenyl-4-nitro-3-pyridinesulfonamide, N-aryl-4-nitro-3-pyridinesulfonamide, N-acyl-4-nitro-3-pyridinesulfonamide, N,N-dialkyl-4-nitro-3-pyridinesulfonamide, 3-(N-benzylamino)-4-nitropyridine, N-benzyl-4-nitro-3- pyridinesulfonamide, N-benzyl-4-nitro-3-pyridinecarboxamide and isomers of the above 3-substituted-4-nitropyridines, isomers having a substituent on the 2-position instead of the 3-position, 2-nitroquinoline, 4-halogeno-2-nitro quinoline, 4-cyano-2-nitroquinoline, 4-aryl-2-nitroquinoline, 4-alkyl-2-nitroquinoline, 4-alkenyl-2-nitroquinoline, 4-hydroxy-2-nitroquinoline, 4-alkoxy-2-nitroquinoline, 4-alkenyloxy-2-nitroquinoline, 4-aryloxy-2-nitroquinoline, 4-benzyloxy-2-nitroquinoline, 4-acyloxy-2-nitroquinoline, 4-amino-2-nitroquinoline, 4-(N-alkylamino)-2-nitroquinoline, 4-(N-alkenylamino)-2-nitroquinoline, 4-(N-arylamino)-2-nitroquinoline, 4-(N-acylamino)-2-nitroquinoline, 4-(N,N-dialkylamino)-2-nitroquinoline, 2,4-dinitroquinoline, 4-benzyl-2-nitroquinoline, 2-nitro-4-quinolinecarboxylic acid, 4-aryloxycarbonyl-2-nitroquinoline, 4-benzyloxycarbonyl-2-nitroquinoline, 4-mercapto-2-nitroquinoline, 4-alkylthio-2-nitroquinoline, 4-alkenylthio-2-nitroquinoline, 4-arylthio-2-nitroquinoline, 4-benzylthio-2-nitroquinoline, 4-acylthio-2-nitroquinoline, 2-nitro-4-quinolinesulfonic acid, alkyl 2-nitro-4-quinolinesulfonate, alkenyl 2-nitro-4-quinolinesulfonate, aryl 2-nitro-4-quinolinesulfonate benzyl 2-nitro-4-quinolinesulfonate, 4-trifluoromethyl-2-nitroquinoline, 4-chloromethyl-2-nitroquinoline, 4-(2-methoxyethyl)-2-nitroquinoline, 4-trifluoromethoxy-2-nitroquinoline, 4-difluoromethoxy-2-nitroquinoline, 4-(2-methoxyethoxy)-2-nitroquinoline, 4-(2-chlorovinyl)-2-nitroquinoline, 4-(α-styryl)-2-nitroquinoline, 4-(3-methoxy-1-propenyl)-2-nitroquinoline, 4-cycloalkyl-2-nitroquinoline, 4-fluorocyclopropyl-2-nitroquinoline, 4-(2-oxazolinyl)-2-nitroquinoline, 4-(4-piperidyl)-2-nitroquinoline, 4-alkylsulfonyl-2-nitroquinoline, 4-alkenylsulfonyl-2-nitroquinoline, 4-arylsulfonyl-2-nitroquinoline, 4-benzylsulfonyl-2-nitroquinoline, 2-nitro-4-quinolinecarboxamide, N-alkyl-2-nitro-4-quinolinecarboxamide, N-alkenyl-2-nitro-4-quinolinecarboxamide, N-aryl-2-nitro-4-quinolinecarboxamide, N-acyl-2-nitro-4-quinolinecarboxamide, N,N-dialkyl-2-nitro-4-quinolinecarboxamide, 2-nitro-4-quinolinesulfonamide, N-alkyl-2-nitro-4-quinolinesulfonamide, N-alkenyl-2-nitro-4-quinolinesulfonamide, N-aryl-2-nitro-4-quinolinesulfonamide, N-acyl-2-nitro-4-quinolinesulfonamide, N,N-dialkyl-2-nitro-4-quinolinesulfonamide, 4-acetyl-2-nitro quinoline, 4-alkenylcarbonyl-2-nitroquinoline, 4-arylcarbonyl-2-nitroquinoline, 4-benzylcarbonyl-2-nitroquinoline, 4-alkoxycarbonyl-2-nitroquinoline, 4-alkenyloxycarbonyl-2-nitroquinoline, 4-(N-benzylamino)-2-nitroquinoline, N-benzyl-2-nitro-4-quinolinesulfonamide, N-benzyl-2-nitro-4-quinolinecarboxamide, 3-nitroquinoline, 4-halogeno-3-nitroquinoline, 4-cyano-3-nitroquinoline, 4-aryl-3-nitroquinoline, 4-alkyl-3-nitroquinoline, 4-alkenyl-3-nitroquinoline, 4-hydroxy-3-nitroquinoline, 4-alkoxy-3-nitroquinoline, 4-alkenyloxy-3-nitroquinoline, 4-aryloxy-3-nitroquinoline, 4-benzyloxy-3-nitroquinoline, 4-acyloxy-3-nitroquinoline, 4-amino-3-nitroquinoline, 4-(N-alkylamino)-3-nitroquinoline, 4-(N-alkenylamino)-3-nitroquinoline, 4-(N-arylamino)-3-nitroquinoline, 4-(N-acylamino)-3-nitroquinoline, 4-(N,N-dialkylamino)-3-nitroquinoline, 3,4-dinitroquinoline, 4-benzyl-3-nitroquinoline, 3-nitro-4-quinolinecarboxylic acid, 4-aryloxycarbonyl-3-nitroquinoline, 4-benzyloxycarbonyl-3-nitroquinoline, 4-mercapto-3-nitroquinoline, 4-alkylthio-3-nitroquinoline, 4-alkenylthio-3-nitroquinoline, 4-arylthio-3-nitroquinoline, 4-benzylthio-3-nitroquinoline, 4-acylthio-3-nitroquinoline, 3-nitro-4-quinolinesulfonic acid, alkyl 3-nitro-4-quinolinesulfonate, alkenyl-3-nitro-4-quinolinesulfonate, aryl 3-nitro-4- quinolinesulfonate, benzyl 3-nitro-4-quinolinesulfonate, 4-trifluoromethyl-3-nitroquinoline, 4-chloromethyl-3-nitroquinoline, 4-(2-methoxyethyl)-3-nitroquinoline, 4-trifluoromethoxy-3-nitroquinoline, 4-difluoromethoxy-3-nitroquinoline, 4-(2-methoxyethoxy)-3-nitroquinoline, 4-(2-chlorovinyl)-3-nitroquinoline, 4-(α-styryl)-3-nitroquinoline, 4-(3-methoxy-1-propenyl)-3-nitroquinoline, 4-cycloalkyl-3-nitroquinoline, 4-fluorocyclopropyl-3-nitroquinoline, 4-(2-oxazolinyl)-3-nitroquinoline, 4-(4-piperidyl)-3-nitroquinoline, 4-alkylsulfonyl-3-nitroquinoline, 4-alkenylsulfonyl-3-nitroquinoline, 4-arylsulfonyl-3-nitroquinoline, 4-benzylsulfonyl-3-nitroquinoline, 3-nitro4-quinolinecarboxamide, N-alkyl-3-nitro-4-quinolinecarboxamide, N-alkenyl-3-nitro-4-quinolinecarboxamide, N-aryl-3-nitro-4-quinolinecarboxamide, N-acyl-3-nitro-4-quinolinecarboxamide, N,N-dialkyl-3-nitro-4-quinolinecarboxamide, 3-nitro-4-quinolinesulfonamide, N-alkyl-3-nitro-4-quinolinesulfonamide, N-alkenyl-3-nitro-4-quinolinesulfonamide, N-aryl-3-nitro-4-quinolinesulfonamide, N,N-3-nitro-4-quinolinesulfonamide, N,N-dialkyl-3-nitro-4-quinolinesulfonamide, 4-acetyl-3-nitroquinoline, 4-alkenylcarbonyl-3-nitroquinoline, 4-arylcarbonyl-3-nitroquinoline, 4-benzylcarbonyl-3-nitroquinoline, 4-alkoxycarbonyl-3-nitroquinoline, 4-alkenyloxycarbonyl-3-nitroquinoline, 4-(N-benzylamino)-3-nitroquinoline, N-benzyl-3-nitro-4-quinolinesulfonamide, N-benzyl-3-nitro-4-quinolinecarboxamide and isomers of the above 4-substituted-3-nitroquinolines, isomers having a substituent on the 2-position instead of the 4-position, 4-nitroquinoline, 2-halogeno-4-nitroquinoline, 2-cyano-4-nitroquinoline, 2-aryl-4-nitroquinoline, 2-alkyl-4-nitroquinoline, 2-alkenyl-4-nitroquinoline, 2-hydroxy-4-nitroquinoline, 2-alkoxy-4-nitroquinoline, 2-alkenyloxy-4-nitroquinoline, 2-aryloxy-4-nitroquinoline, 2-benzyloxy-4-nitroquinoline, 2-acyloxy-4-nitroquinoline, 2-amino-4-nitroquinoline, 2-(N-alkylamino)-4-nitroquinoline, 2-(N-alkenylamino)-4-nitroquinoline, 2-(N-arylamino)-4-nitroquinoline, 2-(N-acylamino)- 4-nitroquinoline, 2-(N,N- dialkylamino)-4-nitroquinoline, 2,4-dinitroquinoline, 2-benzyl-4-nitroquinoline, 4-nitro-2-quinolinecarboxylic acid, 2-aryloxycarbonyl-4-nitroquinoline, 2-benzyloxycarbonyl-4-nitroquinoline, 2-mercapto-4-nitroquinoline, 2-alkylthio-4-nitroquinoline, 2-alkenylthio-4-nitroquinoline, 2-arylthio-4-nitroquinoline, 2-benzylthio-4-nitro quinoline, 2-acylthio-4-nitro quinoline, 4-nitro-2-quinolinesulfonic acid, alkyl 4-nitro-2-quinolinesulfonate, alkenyl 4-nitro-2-quinolinesulfonate, aryl 4-nitro-2-quinolinesulfonate, benzyl 4-nitro-2-quinolinesulfonate, 2-trifluoromethyl-4-nitroquinoline, 2-chloromethyl-4-nitroquinoline, 2-(2-methoxyethyl)-4-nitroquinoline, 2-trifluoromethoxy-4-nitroquinoline, 2-difluoromethoxy-4-nitroquinoline, 2-(2-methoxyethoxy)-4-nitroquinoline, 2-(2-chlorovinyl)-4-nitroquinoline, 2-(α-styryl)-4-nitroquinoline, 2-(3-methoxy-1-propenyl)-4-nitroquinoline, 2-cycloalkyl-4-nitroquinoline, 2-fluorocyclopropyl-4-nitroquinoline, 2-(2-oxazolinyl)-4-nitroquinoline, 2-(4-piperidyl)-4-nitroquinoline, 2-alkylsulfonyl-4-nitroquinoline, 2-alkenylsulfonyl-4-nitroquinoline, 2-arylsulfonyl-4-nitroquinoline, 2-benzylsulfonyl-4-nitroquinoline, 4-nitro-2-quinolinecarboxamide, N-alkyl-4-nitro-2-quinolinecarboxamide, N-alkenyl-4-nitro-2-quinolinecarboxamide, N-aryl-4-nitro-2-quinolinecarboxamide, N-acyl-4-nitro-2-quinolinecarboxamide, N,N-dialkyl-4-nitro-2-quinolinecarboxamide, 4-nitro-2-quinolinesulfonamide, N-alkyl-4-nitro-2-quinolinesulfonamide, N-alkenyl-4-nitro-2-quinolinesulfonamide, N-aryl-4-nitro-2-quinolinesulfonamide, N-acyl-4-nitro-2-quinolinesulfonamide, N,N-dialkyl-4-nitro-2-quinolinesulfonamide, 2-acetyl-4-nitroquinoline, 2-alkenylcarbonyl-4-nitroquinoline, 2-arylcarbonyl-4-nitroquinoline, 2-benzylcarbonyl-4-nitroquinoline, 2-alkoxycarbonyl-4-nitroquinoline, 2-alkenyloxycarbonyl-4-nitroquinoline, 2-(N-benzylamino)-4-nitroquinoline, N-benzyl-4-nitro-2-quinolinesulfonamide, N-benzyl-4-nitro-2-quinolinecarboxamide, furthermore, compounds having a 5, 6, 7, 8-tetrahydroquinoline ring, a 5, 6, 7, 8-tetrahydro[1,6] naphthyridine ring, a 7, 8-dihydro-5H-pyrano[4,3-b]pyridine ring or a 7, 8-dihydro-5H-thiopyrano[4,3-b]pyridine ring instead of a quinoline ring of the above quinoline derivatives, etc.

In addition, compounds having a N-oxide unit instead of a nitrogen atom of the 1-position in all the above pyridine derivatives and quinoline derivatives are also included.

Examples of the aminonitropyridine represented by the general formula [1] include 5-amino-2-nitropyridine, 5-amino-3-halogeno-2-nitropyridine, 5-amino-3-cyano-2-nitropyridine, 5-amino-3-aryl-2-nitropyridine, 5-amino-3-alkyl-2-nitropyridine, 5-amino-3-alkenyl-2-nitropyridine, 5-amino-3-hydroxy-2-nitropyridine, 5-amino-3-alkoxy-2-nitropyridine, 5-amino-3-alkenyloxy-2-nitropyridine, 5-amino-3-aryloxy-2-nitropyridine, 5-amino-3-benzyloxy-2-nitropyridine, 5-amino-3-acyloxy-2-nitropyridine, 3,5-diamino-2-nitropyridine, 5-amino-3-(N-alkylamino)-2-nitropyridine, 5-amino-3-(N-alkenylamino)-2-nitropyridine, 5-amino-3-(N-arylamino)-2-nitropyridine, 5-amino-3-(N-acylamino)-2-nitropyridine, 5-amino-3-(N,N-dialkylamino)-2-nitropyridine, 5-amino-3-acetyl-2-nitropyridine, 5-amino-3-alkenylcarbonyl-2-nitropyridine, 5-amino-3-arylcarbonyl-2-nitropyridine, 5-amino-3-benzylcarbonyl-2-nitropyridine, 5-amino-3-alkoxycarbonyl-2-nitropyridine, 5-amino-3-alkenyloxycarbonyl-2-nitropyridine, 5-amino-2,3-dinitropyridine, 5-amino-3-benzyl-2-nitropyridine, 5-amino-2-nitro-3-pyridinecarboxylic acid, 5-amino-3-aryloxycarbonyl-2-nitropyridine, 5-amino-3-benzyloxycarbonyl-2-nitropyridine, 5-amino-3-mercapto-2-nitropyridine, 5-amino-3-alkylthio-2-nitropyridine, 5-amino-3-alkenylthio-2-nitropyridine, 5-amino-3-arylthio-2-nitropyridine, 5-amino-3-benzylthio-2-nitropyridine, 5-amino-3-acylthio-2-nitropyridine, 5-amino-2-nitro-3-pyridinesulfonic acid, alkyl 5-amino-2-nitro-3-pyridinesulfonate, alkenyl 5-amino-2-nitro-3-pyridinesulfonate, aryl 5-amino-2-nitro-3-pyridinesulfonate, benzyl 5-amino-2-nitro-3-pyridinesulfonate, 5-amino-3-trifluoromethyl-2-nitropyridine, 5-amino-3-chloromethyl-2-nitropyridine, 5-amino-3-(2-methoxyethyl)-2-nitropyridine, 5-amino-3-trifluoromethoxy-2-nitropyridine, 5-amino-3-difluoromethoxy-2-nitropyridine, 5-amino-3-(2-methoxyethoxy)-2-nitropyridine, 5-amino-3-(2-chlorovinyl)-2-nitropyridine, 5-amino-3-(a-styryl)-2-nitropyridine, 5-amino-3-(3-methoxy-1-propenyl)-2-nitropyridine, 5-amino-3-cycloalkyl-2-nitropyridine, 5-amino-3-fluorocyclopropyl-2-nitropyridine, 5-amino-3-(2-oxazolinyl)-2-nitropyridine, 5-amino-3-(4-piperidyl)-2-nitropyridine, 5-amino-3-(alkylsulfonyl)-2-nitropyridine, 5-amino-3-alkenylsulfonyl-2-nitropyridine, 5-amino-3-arylsulfonyl-2-nitropyridine, 5-amino-3-benzylsulfonyl-2-nitropyridine, 5-amino-2-nitro-3-pyridinecarboxamide, N-alkyl-5-amino-2-nitro-3-pyridinecarboxamide, N-alkenyl-5-amino-2-nitro-3-pyridinecarboxamide, N-aryl-5-amino-2-nitro-3-pyridinecarboxamide, N-acyl-5-amino-2-nitro-3-pyridinecarboxamide, N,N-dialkyl-5-amino-2-nitro-3-pyridinecarboxamide, 5-amino-2-nitro-3-pyridinesulfonamide, N-alkyl-5-amino-2-nitro-3-pyridinesulfonamide, N-alkenyl-5-amino-2-nitro-3-pyridinesulfonamide, N-aryl-5-amino-2-nitro-3-pyridinesulfonamide, N-acyl-5-amino-2-nitro-3-pyridinesulfonamide, N,N-dialkyl-5-amino-2-nitro-3-pyridinesulfonamide, 5-amino-3-(N-benzylamino)-2-nitropyridine, N-benzyl-5-amino-2-nitro-3-pyridinesulfonamide, N-benzyl-5-amino-2-nitro-3-pyridinecarboxamide and isomers of the above 5-amino-3-substituted-2-nitropyridines, the isomers having a substituent on the 4-or 6-position instead of the 3-position, 3-amino-2-nitropyridine, 3-amino-4-halogeno-2-nitropyridine, 3-amino-4-cyano-2-nitropyridine, 3-amino-4-aryl-2-nitropyridine, 3-amino-4-alkyl-2-nitropyridine, 3-amino-4-alkenyl-2-nitropyridine, 3-amino-4-hydroxy-2-nitropyridine, 3-amino-4-alkoxy-2-nitropyridine, 3-amino-4-alkenyloxy-2-nitropyridine, 3-amino-4-aryloxy-2-nitropyridine, 3-amino-4-benzyloxy-2-nitropyridine, 3-amino-4-acyloxy-2-nitropyridine, 3,4-diamino-2-nitropyridine, 3-amino-4-(N-alkylamino)-2-nitropyridine, 3-amino-4-(N-alkenylamino)-2-nitropyridine, 3-amino-4-(N-arylamino)-2-nitropyridine, 3-amino-4-(N-acylamino)-2-nitropyridine, 3-amino-4-(N,N-dialkylamino)-2-nitropyridine, 3-amino-4-acetyl-2-nitropyridine, 3-amino-4-alkenylcarbonyl-2-nitropyridine, 3-amino-4-arylcarbonyl-2-nitropyridine, 3-amino-4-benzylcarbonyl-2-nitropyridine, 3-amino-4-alkoxycarbonyl-2-nitropyridine, 3-amino-4-alkenyloxycarbonyl-2-nitropyridine, 3-amino-2,4-dinitropyridine, 3-amino-4-benzyl-2-nitropyridine, 3-amino-2-nitro-4-pyridinecarboxylic acid, 3-amino-4-aryloxycarbonyl-2-nitropyridine, 3-amino-4-benzyloxycarbonyl-2-nitropyridine, 3-amino-4-mercapto-2-nitropyridine, 3-amino-4-alkylthio-2-nitropyridine, 3-amino-4-alkenylthio-2-nitropyridine, 3-amino-4-arylthio-2-nitropyridine, 3-amino-4-benzylthio-2-nitropyridine, 3-amino-4-acylthio-2-nitropyridine, 3-amino-2-nitro-4-pyridinesulfonic acid, alkyl 3-amino-2-nitro-4-pyridinesulfonate, alkenyl 3-amino-2-nitro-4-pyridinesulfonate, aryl 3-amino-2-nitro-4-pyridinesulfonate, benzyl 3-amino-2-nitro-4-pyridinesulfonate, 3-amino-4-trifluoromethyl-2-nitropyridine, 3-amino-4-chloromethyl-2-nitropyridine, 3-amino-4-(2-methoxyethyl)-2-nitropyridine, 3-amino-4-trifluoromethoxy-2-nitropyridine, 3-amino-4-difluoromethoxy-2-nitropyridine, 3-amino-4-(2-methoxyethoxy)-2-nitropyridine, 3-amino-4-(2-chlorovinyl)-2-nitropyridine, 3-amino-4-(α-styryl)-2-nitropyridine, 3-amino-4-(3-methoxy-1-propenyl)-2-nitropyridine, 3-amino-4-cycloalkyl-2-nitropyridine, 3-amino-4-fluorocyclopropyl-2-nitropyridine, 3-amino-4-(2-oxazolinyl)-2-nitropyridine, 3-amino-4-(4-piperidyl)-2-nitropyridine, 3-amino-4-alkylsulfonyl-2-nitropyridine, 3-amino-4-alkenylsulfonyl-2-nitropyridine, 3-amino-4-arylsulfonyl-2-nitropyridine, 3-amino-4-benzylsulfonyl-2-nitropyridine, 3-amino-2-nitro-4-pyridinecarboxamide, N-alkyl-3-amino-2-nitro-4-pyridinecarboxamide, N-alkenyl-3-amino-2-nitro-4-pyridinecarboxamide, N-aryl-3-amino-2-nitro-4-pyridinecarboxamide, N-aryl-3-amino-2-nitro-4-pyridinecarboxamide, N,N-dialkyl-3-amino-2-nitro-4-pyridinecarboxamide, 3-amino-2-nitro-4-pyridinesulfonamide, N-alkyl-3-amino-2-nitro-4-pyridinesulfonamide, N-alkenyl-3-amino-2-nitro-4-pyridinesulfonamide, N-aryl-3-amino-2-nitro-4-pyridinesulfonamide, N-acyl-3-amino-2-nitro-4-pyridinesulfonamide, N,N-dialkyl-3-amino-2-nitro-4-pyridinesulfonamide, 3-amino-4-(N-benzylamino)-2-nitropyridine, N-benzyl-3-amino-2-nitro-4-pyridinesulfonamide, N-benzyl-3-amino-2-nitro-4-pyridinecarboxamide and isomers of the above 3-amino-4-substituted-2-nitropyridines, the isomers having a substituent on the 5- or 6-position instead of 4-position, 4-amino-3-nitropyridine, 4-amino-2-halogeno-3-nitropyridine, 4-amino-2-cyano-3-nitropyridine, 4-amino-2-aryl-3-nitropyridine, 4-amino-2-alkyl-3-nitropyridine, 4-amino-2-alkenyl-3-nitropyridine, 4-amino-2-hydroxy-3-nitropyridine, 4-amino-2-alkoxy-3-nitropyridine, 4-amino-2-alkenyloxy-3-nitropyridine, 4-amino-2-aryloxy-3-nitropyridine, 4-amino-2-benzyloxy-3-nitropyridine, 4-amino-2-acyloxy-3-nitropyridine, 2,4-diamino-3-nitropyridine, 4-amino-2-(N-alkylamino)-3-nitropyridine, 4-amino-2-(N-alkenylamino)-3-nitropyridine, 4-amino-2-(N-arylamino)-3-nitropyridine, 4-amino-2-(N-acylamino)-3-nitropyridine, 4-amino-2-(N,N-dialkylamino)-3-nitropyridine, 4-amino-2-acetyl-3-nitropyridine, 4-amino-2-alkenylcarbonyl-3-nitropyridine, 4-amino-2-arylcarbonyl-3-nitropyridine, 4-amino-2-benzylcarbonyl-3-nitropyridine, 4-amino-2-alkoxycarbonyl-3-nitropyridine, 4-amino-2-alkenyloxycarbonyl-3-nitropyridine, 4-amino-2,3-dinitropyridine, 4-amino-2-benzyl-3-nitropyridine, 4-amino-3-nitro-2-pyridinecarboxylic acid, 4-amino-2-aryloxycarbonyl-3-nitropyridine, 4-amino-2-benzyloxycarbonyl-3-nitropyridine, 4-amino-2-mercapto-3-nitropyridine, 4-amino-2-alkylthio-3-nitropyridine, 4-amino-2-alkenylthio-3-nitropyridine, 4-amino-2-arylthio-3-nitropyridine, 4-amino-2-benzylthio-3-nitropyridine, 4-amino-2-acylthio-3-nitropyridine, 4-amino-3-nitro-2-pyridinesulfonic acid, alkyl 4-amino-3-nitro-2-pyridinesulfonate, alkenyl 4-amino-3-nitro-2-pyridinesulfonate, aryl 4-amino-3-nitro-2-pyridinesulfonate, benzyl 4-amino-3-nitro-2-pyridinesulfonate, 4-amino-2-trifluoromethyl-3-nitropyridine, 4-amino-2-chloromethyl-3-nitropyridine, 4-amino-2-(2-methoxyethyl)-3-nitropyridine, 4-amino-2-trifluoromethoxy-3-nitropyridine, 4-amino-2-difluoromethoxy-3-nitropyridine, 4-amino-2-(2-methoxyethoxy)-3-nitropyridine, 4-amino-2-(2-chlorovinyl)-3-nitropyridine, 4-amino-2-(α-styryl)-3-nitropyridine, 4-amino-2-(3-methoxy-1-propenyl)-3-nitropyridine, 4-amino-2-cycloalkyl-3-nitropyridine, 4-amino-2-fluorocyclopropyl-3-nitropyridine, 4-amino-2-(2-oxazolinyl)-3-nitropyridine, 4-amino-2-(4-piperidyl)-3-nitropyridine, 4-amino-2-alkylsulfonyl-3-nitropyridine, 4-amino-2-alkenylsulfonyl-3-nitropyridine, 4-amino-2-arylsulfonyl-3-nitropyridine, 4-amino-2-benzylsulfonyl-3-nitropyridine, 4-amino-3-nitro-2-pyridinecarboxamide, N-alkyl-4-amino-3-nitro-2-pyridinecarboxamide, N-alkenyl-4-amino-3-nitro-2-pyridinecarboxamide, N-aryl-4-amino-3-nitro-2-pyridinecarboxamide, N-acyl-4-amino-3-nitro-2-pyridinecarboxamide, N,N-dialkyl-4-amino-3-nitro-2-pyridinecarboxamide, 4-amino-3-nitro-2-pyridinesulfonamide, N-alkyl-4-amino-3-nitro-2-pyridinesulfonamide, N-alkenyl-4-amino-3-nitro-2-pyridinesulfonamide, N-aryl-4-amino-3-nitro-2-pyridinesulfonamide, N-acyl-4-amino-3-nitro-2-pyridinesulfonamide, N,N-dialkyl-4-amino-3-nitro-2-pyridinesulfonamide, 4-amino-2-(N-benzylamino)-3-nitropyridine, N-benzyl-4-amino-3-nitro-2-pyridinesulfonamide, N-benzyl-4-amino-3-nitro-2-pyridinecarboxamide and isomers of the above 4-amino-2-substituted-3-nitropyridines, the isomers having a substituent on the 5- or 6-position instead of the 2-position, 2-amino-3-nitropyridine, 2-amino-4-halogeno-3-nitropyridine, 2-amino-4-cyano-3-nitropyridine, 2-amino-4-aryl-3-nitropyridine, 2-amino-4-alkyl-3-nitropyridine, 2-amino-4-alkenyl-3-nitropyridine, 2-amino-4-hydroxy-3-nitropyridine, 2-amino-4-alkoxy-3-nitropyridine, 2-amino-4-alkenyloxy-3-nitropyridine, 2-amino-4-aryloxy-3-nitropyridine, 2-amino-4-benzyloxy-3-nitropyridine, 2-amino-4-acyloxy-3-nitropyridine, 2,4-diamino-3-nitropyridine, 2-amino-4-(N-alkylamino)-3-nitropyridine, 2-amino-4-(N-alkenylamino)-3-nitropyridine, 2-amino-4-(N-arylamino)-3-nitropyridine, 2-amino-4-(N-acylamino)-3-nitropyridine, 2-amino-4-(N,N-dialkylamino)-3-nitropyridine, 2-amino-4-acetyl-3-nitropyridine, 2-amino-4-alkenylcarbonyl-3-nitropyridine, 2-amino-4-arylcarbonyl-3-nitropyridine, 2-amino-4-benzylcarbonyl-3-nitropyridine, 2-amino-4-alkoxycarbonyl-3-nitropyridine, 2-amino-4-alkenyloxycarbonyl-3-nitropyridine, 2-amino-3,4-dinitropyridine, 2-amino-4-benzyl-3-nitropyridine, 2-amino-3-nitro-4-pyridinecarboxylic acid, 2-amino-4-aryloxycarbonyl-3-nitropyridine, .2-amino-4-benzyloxycarbonyl-3-nitropyridine, 2-amino-4-mercapto-3-nitropyridine, 2-amino-4-alkylthio-3-nitropyridine, 2-amino-4-alkenylthio-3-nitropyridine, 2-amino-4-arylthio-3-nitropyridine, 2-amino-4-benzylthio-3-nitropyridine, 2-amino-4-acylthio-3-nitropyridine, 2-amino-3-nitro-4-pyridinesulfonic acid, alkyl 2-amino-3-nitro-4-pyridinesulfonate, alkenyl 2-amino-3-nitro-4-pyridinesulfonate, aryl 2-amino-3-nitro-4-pyridinesulfonate, benzyl 2-amino-3-nitro-4-pyridinesulfonate, 2-amino-4-trifluoromethyl-3-nitropyridine, 2-amino-4-chloromethyl-3-nitropyridine, 2-amino-4-(2-methoxyethyl)-3-nitropyridine, 2-amino-4-trifluoromethoxy-3-nitropyridine, 2-amino-4-difluoromethoxy-3-nitropyridine, 2-amino-4-(2-methoxyethoxy)-3-nitropyridine, 2-amino-4-(2-chlorovinyl)-3-nitropyridine, 2-amino-4-(α-styryl)-3-nitropyridine, 2-amino-4-(3-methoxy-1-propenyl)-3-nitropyridine, 2-amino4-cycloalkyl-3-nitropyridine, 2-amino-4-fluorocyclopropyl-3-nitropyridine, 2-amino-4-(2-oxazolinyl)-3-nitropyridine, 2-amino-4-(4-piperidyl)-3-nitropyridine, 2-amino-4-alkylsulfonyl-3-nitropyridine, 2-amino-4-alkenylsulfonyl-3-nitropyridine, 2-amino-4-arylsulfonyl-3-nitropyridine, 2-amino-4-benzylsulfonyl-3-nitropyridine, 2-amino-3-nitro-4-pyridinecarboxamide, N-alkyl-2-amino-3-nitro-4-pyridinecarboxamide, N-alkenyl-2-amino-3-nitro-4-pyridinecarboxamide, N-aryl-2-amino-3-nitro-4-pyridinecarboxamide, N-acyl-2-amino-3-nitro-4-pyridinecarboxamide, N,N-dialkyl-2-amino-3-nitro-4-pyridinecarboxamide, 2-amino-3-nitro-4-pyridinesulfonamide, N-alkyl-2-amino-3-nitro-4-pyridinesulfonamide, N-alkenyl-2-amino-3-nitro-4-pyridinesulfonamide, N-aryl-2-amino-3-nitro-4-pyridinesulfonamide, N-acyl-2-amino-3-nitro-4-pyridinesulfonamide, N,N-dialkyl-2-amino-3-nitro-4-pyridinesulfonamide, 2-amino-4-(N-benzylamino)-3-nitropyridine, N-benzyl-2-amino-3-nitro-4-pyridinesulfonamide, N-benzyl-2-amino-3-nitro-4-pyridinecarboxamide and isomers of the above 2-amino-4-substituted-3-nitropyridines, the isomers having a substituent on the 5- or 6-position instead of the 4-position, 6-amino-3-nitropyridine, 6-amino-4-halogeno-3-nitropyridine, 6-amino-4-cyano-3-nitropyridine, 6-amino-4-aryl-3-nitropyridine, 6-amino-4-alkyl-3-nitropyridine, 6-amino-4-alkenyl-3-nitropyridine, 6-amino-4-hydroxy-3-nitropyridine, 6-amino-4-alkoxy-3-nitropyridine, 6-amino-4-alkenyloxy-3-nitropyridine, 6-amino-4-aryloxy-3-nitropyridine, 6-amino-4-benzyloxy-3-nitropyridine, 6-amino-4-acyloxy-3-nitropyridine, 4,6-diamino-3-nitropyridine, 6-amino-4-(N-alkylamino)-3-nitropyridine, 6-amino-4-(N-alkenylamino)-3-nitropyridine, 6-amino-4-(N-arylamino)-3-nitropyridine, 6-amino-4-(N-arylamino)-3-nitropyridine, 6-amino-4-(N,N-dialkylamino)-3-nitropyridine, 6-amino-4-acetyl-3-nitropyridine, 6-amino-4-alkenylcarbonyl-3-nitropyridine, 6-amino-4-arylcarbonyl-3-nitropyridine, 6-amino-4-benzylcarbonyl-3-nitropyridine, 6-amino-4-alkoxycarbonyl-3-nitropyridine, 6-amino-4-alkenyloxycarbonyl-3-nitropyridine, 6-amino-3,4-dinitropyridine, 6-amino-4-benzyl-3-nitropyridine, 6-amino-3-nitro-4-pyridinecarboxylic acid, 6-amino-4-aryloxycarbonyl-3-nitropyridine, 6-amino-4-benzyloxycarbonyl-3-nitropyridine, 6-amino-4-mercapto-3-nitropyridine, 6-amino-4-alkylthio-3-nitropyridine, 6-amino-4-alkenylthio-3-nitropyridine, 6-amino-4-arylthio-3-nitropyridine, 6-amino-4-benzylthio-3-nitropyridine, 6-amino-4-acylthio-3-nitropyridine, 6-amino-3-nitro-4-pyridinesulfonic acid, alkyl 6-amino-3-nitro-4-pyridinesulfonate, alkenyl 6-amino-3-nitro-4-pyridinesulfonate, aryl 6-amino-3-nitro-4-pyridinesulfonate, benzyl 6-amino-3-nitro-4-pyridinesulfonate, 6-amino-4-trifluoromethyl-3-nitropyridine, 6-amino-4-chloromethyl-3-nitropyridine, 6-amino-4-(2-methoxyethyl)-3-nitropyridine, 6-amino-4-trifluoromethoxy-3-nitropyridine, 6-amino-4-difluoromethoxy-3-nitropyridine, 6-amino-4-(2-methoxyethoxy)-3-nitropyridine, 6-amino-4-(2-chlorovinyl)-3-nitropyridine, 6-amino-4-(α-styryl)-3-nitropyridine, 6-amino-4-(3-methoxy-1-propenyl)-3-nitropyridine, 6-amino-4-cycloalkyl-3-nitropyridine, 6-amino-4-fluorocyclopropyl-3-nitropyridine, 6-amino-4-(2-oxazolinyl)-3-nitropyridine, 6-amino-4-(4-piperidyl)-3-nitropyridine, 6-amino-4-alkylsulfonyl-3-nitropyridine, 6-amino-4-alkenylsulfonyl-3-nitropyridine, 6-amino-4-arylsulfonyl-3-nitropyridine, 6-amino-4-benzylsulfonyl-3-nitropyridine, 6-amino-3-nitro-4-pyridinecarboxamide, N-alkyl-6-amino-3-nitro-4-pyridinecarboxamide, N-alkenyl-6-amino-3-nitro-4-pyridinecarboxamide, N-aryl-6-amino-3-nitro-4-pyridinecarboxamide, N-acyl-6-amino-3-nitro-4-pyridinecarboxamide, N,N-dialkyl-6-amino-3-nitro-4-pyridinecarboxamide, 6-amino-3-nitro-4-pyridinesulfonamide, N-alkyl-6-amino-3-nitro-4-pyridinesulfonamide, N-alkenyl-6-amino-3-nitro-4-pyridinesulfonamide, N-aryl-6-amino-3-nitro-4-pyridinesulfonamide, N-acyl-6-amino-3-nitro-4-pyridinesulfonamide, N,N-dialkyl-6-amino-3-nitro-4-pyridinesulfonamide, 6-amino-4-(N-benzylamino)-3-nitropyridine, N-benzyl-6-amino-3-nitro-4-pyridinesulfonamide, N-benzyl- 6-amino-3-nitro-4-pyridinecarboxamide and isomers of the 6-amino-4-substituted-3-nitropyridines, the isomers having a substituent on the 2- or 5-position instead of the 4-position, 3-amino-4-nitropyridine, 3-amino-5-halogeno-4-nitropyridine, 3-amino-5-cyano-4-nitropyridine, 3-amino-5-aryl-4-nitropyridine, 3-amino-5-alkyl-4-nitropyridine, 3-amino-5-alkenyl-4-nitropyridine, 3-amino-5-hydroxy-4-nitropyridine, 3-amino-5-alkoxy-4-nitropyridine, 3-amino-5-alkenyloxy-4-nitropyridine, 3-amino-5-aryloxy-4-nitropyridine, 3-amino-5-benzyloxy-4-nitropyridine, 3-amino-5-acyloxy-4-nitropyridine, 3,5-diamino-4-nitropyridine, 3-amino-5-(N-alkylamino)-4-nitropyridine, 3-amino-5-(N-alkenylamino)-4-nitropyridine, 3-amino-5-(N-arylamino)-4-nitropyridine, 3-amino-5-(N-acylamino)-4-nitropyridine, 3-amino-5-(N,N-dialkylamino)-4-nitropyridine, 3-amino-5-acetyl-4-nitropyridine, 3-amino-5-alkenylcarbonyl-4-nitropyridine, 3-amino-5-arylcarbonyl-4-nitropyridine, 3-amino-5-benzylcarbonyl-4-nitropyridine, 3-amino-5-alkoxycarbonyl-4-nitropyridine, 3-amino-5-alkenyloxycarbonyl-4-nitropyridine, 3-amino-4,5-dinitropyridine, 3-amino-5-benzyl-4-nitropyridine, 3-amino-4-nitro-5-pyridinecarboxylic acid, 3-amino-5-aryloxycarbonyl-4-nitropyridine, 3-amino-5-benzyloxycarbonyl-4-nitropyridine, 3-amino-5-mercapto-4-nitropyridine, 3-amino-5-alkylthio-4-nitropyridine, 3-amino-5-alkenylthio-4-nitropyridine, 3-amino-5-arylthio-4-nitropyridine, 3-amino-5-benzylthio-4-nitropyridine, 3-amino-5-acylthio-4-nitropyridine, 3-amino-4-nitro-5-pyridinesulfonic acid, alkyl 3-amino-4-nitro-5-pyridinesulfonate, alkenyl 3-amino-4-nitro-5-pyridinesulfonate, aryl 3-amino-4-nitro-5-pyridinesulfonate, benzyl 3-amino-4-nitro-5-pyridinesulfonate, 3-amino-5-trifluoromethyl-4-nitropyridine, 3-amino-5-chloromethyl-4-nitropyridine, 3-amino-5-(2-methoxyethyl)-4-nitropyridine, 3-amino-5-trifluoromethoxy-4-nitropyridine, 3-amino-5-difluoromethoxy-4-nitropyridine, 3-amino-5-(2-methoxyethoxy)-4-nitropyridine, 3-amino-5-(2-chlorovinyl)-4-nitropyridine, 3-amino-5-(α-styryl)-4-nitropyridine, 3-amino-5-(3-methoxy-1-propenyl)-4-nitropyridine, 3-amino-5-cycloalkyl-4-nitropyridine, 3-amino-5-fluorocyclopropyl-4-nitropyridine, 3-amino-5-(2-oxazolinyl)-4-nitropyridine, 3-amino-5-(4-piperidyl)-4-nitropyridine, 3-amino-5-alkylsulfonyl-4-nitropyridine, 3-amino-5-alkenylsulfonyl-4-nitropyridine, 3-amino-5-arylsulfonyl-4-nitropyridine, 3-amino-5-benzylsulfonyl-4-nitropyridine, 3-amino-4-nitro-5-pyridinecarboxamide, N-alkyl-3-amino-4-nitro-5-pyridinecarboxamide, N-alkenyl-3-amino-4-nitro-5-pyridinecarboxamide, N-aryl-3-amino-4-nitro-5-pyridinecarboxamide, N-acyl-3-amino-4-nitro-5-pyridinecarboxamide, N,N-dialkyl-3-amino-4-nitro-5-pyridinecarboxamide, 3-amino-4-nitro-5-pyridinesulfonamide, N-alkyl-3-amino-4-nitro-5-pyridinesulfonamide, N-alkenyl-3-amino-4-nitro-5-pyridinesulfonamide, N-aryl-3-amino-4-nitro-5-pyridinesulfonamide, N-acyl-3-amino-4-nitro-5-pyridinesulfonamide, N,N-dialkyl-3-amino-4-nitro-5-pyridinesulfonamide, 3-amino-5-(N-benzylamino)-4-nitropyridine, N-benzyl-3-amino-4-nitro-5-pyridinesulfonamide, N-benzyl- 3-amino-4-nitro-5-pyridinecarboxamide and isomers of the above 3-amino-5-substituted-4-nitropyridines, the isomers having a substituent on the 2- or 6-position instead of the 5-position, 3-amino-2-nitroquinoline, 3-amino-4-halogeno-2- nitroquinoline, 3-amino-4-cyano-2-nitroquinoline, 3-amino-4-aryl-2-nitroquinoline, 3-amino-4-alkyl-2-nitroquinoline, 3-amino-4-alkenyl-2-nitroquinoline, 3-amino-4-hydroxy-2-nitroquinoline, 3-amino-4-alkoxy-2-nitroquinoline, 3-amino-4-alkenyloxy-2-nitroquinoline, 3-amino-4-aryloxy-2-nitroquinoline, 3-amino-4-benzyloxy-2-nitroquinoline, 3-amino-4-acyloxy-2-nitroquinoline, 3,4-diamino-2-nitroquinoline, 3-amino-4-(N-alkylamino)-2-nitroquinoline, 3-amino-4-(N-alkenylamino)-2-nitroquinoline, 3-amino-4-(N-arylamino)-2-nitroquinoline, 3-amino-4-(N-acylamino)-2-nitroquinoline, 3-amino-4-(N,N-dialkylamino)-2-nitroquinoline, 3-amino-2,4-dinitroquinoline, 3-amino-4-benzyl-2-nitroquinoline, 3-amino-2-nitro-4-quinolinecarboxylic acid, 3-amino-4-aryloxycarbonyl-2-nitroquinoline, 3-amino-4-benzyloxycarbonyl-2-nitroquinoline, 3-amino-4-mercapto-2-nitroquinoline, 3-amino-4-alkylthio-2-nitroquinoline, 3-amino-4-alkenylthio-2-nitroquinoline, 3-amino-4-arylthio-2-nitroquinoline, 3-amino-4-benzylthio-2-nitroquinoline, 3-amino-4-acylthio-2-nitroquinoline, 3-amino-2-nitro-4-quinolinesulfonic acid, alkyl 3-amino-2-nitro-4-quinolinesulfonate, alkenyl 3-amino-2-nitro-4-quinolinesulfonate, aryl 3-amino-2-nitro-4-quinolinesulfonate, benzyl 3-amino-2-nitro-4-quinolinesulfonate, 3-amino-4-trifluoromethyl-2-nitroquinoline, 3-amino-4-chloromethyl-2-nitroquinoline, 3-amino-4-(2-methoxyethyl)-2-nitroquinoline, 3-amino-4-trifluoromethoxy-2-nitroquinoline, 3-amino-4-difluoromethoxy-2-nitroquinoline, 3-amino-4-(2-methoxyethoxy)-2-nitroquinoline, 3-amino-4-(2-chlorovinyl)-2-nitroquinoline, 3-amino-4-(α-styryl)-2-nitroquinoline, 3-amino-4-(3-methoxy-1-propenyl)-2-nitroquinoline, 3-amino-4-cycloalkyl-2-nitroquinoline, 3-amino-4-fluorocyclopropyl-2-nitroquinoline, 3-amino-4-(2-oxazolinyl)-2-nitroquinoline, 3-amino-4-(4-piperidyl)-2-nitroquinoline, 3-amino-4-alkylsulfonyl-2-nitroquinoline, 3-amino-4-alkenylsulfonyl-2-nitroquinoline, 3-amino-4-arylsulfonyl-2-nitroquinoline, 3-amino-4-benzylsulfonyl-2-nitroquinoline, 3-amino-2-nitro-4-quinolinecarboxamide, N-alkyl-3-amino-2-nitro-4-quinolinecarboxamide, N-alkenyl-3-amino-2-nitro-4-quinolinecarboxamide, N-aryl-3-amino-2-nitro-4-quinolinecarboxamide, N-acyl-3-amino-2-nitro-4-quinolinecarboxamide, N,N-dialkyl-3-amino-2-nitro-4-quinolinecarboxamide, 3-amino-2-nitro-4-quinolinesulfonamide, N-alkyl-3-amino-2-nitro-4-quinolinesulfonamide, N-alkenyl-3-amino-2-nitro-4-quinolinesulfonamide, N-aryl-3-amino-2-nitro-4-quinolinesulfonamide, N-acyl-3-amino-2-nitro-4-quinolinesulfonamide, N,N-dialkyl-3-amino-2-nitro-4-quinolinesulfonamide, 3-amino-4-acetyl-2-nitroquinoline, 3-amino-4-alkenylcarbonyl-2-nitroquinoline, 3-amino-4-arylcarbonyl-2-nitroquinoline, 3-amino-4-benzylcarbonyl-2-nitroquinoline, 3-amino-4-alkoxycarbonyl-2-nitroquinoline, 3-amino-4-alkenyloxycarbonyl-2-nitroquinoline, 3-amino-4-(N-benzylamino)-2-nitroquinoline, N-benzyl-3-amino-2-nitro-4-quinolinesulfonamide, N-benzyl- 3-amino-2-nitro-4-quinolinecarboxamide, 2-amino-3-nitroquinoline, 4-amino-3-nitroquinoline, 2-amino-4-halogeno-3-nitroquinoline, 2-amino-4-cyano-3-nitroquinoline, 2-amino-4-aryl-3-nitroquinoline, 2-amino-4-alkyl-3-nitroquinoline, 2-amino-4-alkenyl-3-nitroquinoline, 2-amino-4-hydroxy-3-nitroquinoline, 2-amino-4-alkoxy-3-nitroquinoline, 2-amino-4-alkenyloxy-3-nitroquinoline, 2-amino-4-aryloxy-3-nitroquinoline, 2-amino-4-benzyloxy-3-nitroquinoline, 2-amino-4-acyloxy-3-nitroquinoline, 2,4-diamino-3-nitroquinoline, 2-amino-4-(N-alkylamino)-3-nitroquinoline, 2-amino-4-(N-alkenylamino)-3-nitroquinoline, 2-amino-4-(N-arylamino)-3-nitroquinoline, 2-amino-4-(N-benzylamino)-3-nitroquinoline, 2-amino-4-(N-acylamino)-3-nitroquinoline, 2-amino-4-(N,N-dialkylamino)-3-nitroquinoline, 2-amino-3,4-dinitroquinoline, 2-amino-4-benzyl-3-nitroquinoline, 2-amino-3-nitro-4-quinolinecarboxylic acid, 2-amino-4-aryloxycarbonyl-3-nitroquinoline, 2-amino-4-benzyloxycarbonyl-3-nitroquinoline, 2-amino-4-mercapto-3-nitroqinoline, 2-amino-4-alkylthio-3-nitroquinoline, 2-amino-4-alkenylthio-3-nitroquinoline, 2-amino-4-arylthio-3-nitroquinoline, 2-amino-4-benzylthio-3-nitroquinoline, 2-amino-4-acylthio-3-nitroquinoline, 2-amino-3-nitro-4-quinolinesulfonic acid, alkyl 2-amino-3-nitro-4-quinolinesulfonate, alkenyl 2-amino-3-nitro-4-quinolinesulfonate, aryl 2-amino-3-nitro-4-quinolinesulfonate, benzyl 2-amino-3-nitro-4-quinolinesulfonate, 2-amino-4-trifluoromethyl-3-nitroquinoline, 2-amino-4-chloromethyl-3-nitroquinoline, 2-amino-4-(2-methoxyethyl)-3-nitroquinoline, 2-amino-4-trifluoromethoxy-3-nitroquinoline, 2-amino-4-difluoromethoxy-3-nitroquinoline, 2-amino-4-(2-methoxyethoxy)-3-nitroquinoline, 2-amino-4-(2-chlorovinyl)-3-nitroquinoline, 2-amino-4-(α-styryl)-3-nitroquinoline, 2-amino-4-(3-methoxy-1-propenyl)-3-nitroquinoline, 2-amino-4-cycloalkyl-3-nitroquinoline, 2-amino-4-fluorocyclopropyl-3-nitroquinoline, 2-amino-4-(2-oxazolinyl)-3-nitroquinoline, 2-amino-4-(4-piperidyl)-3-nitroquinoline, 2-amino-4-alkylsulfonyl-3-nitroquinoline, 2-amino-4-alkenylsulfonyl-3-nitroquinoline, 2-amino-4-arylsulfonyl-3-nitroquinoline, 2-amino-4-benzylsulfonyl-3-nitroquinoline, 2-amino-3-nitro-4-quinolinecarboxamide, N-alkyl-2-amino-3-nitro-4-quinolinecarboxamide, N-alkenyl-2-amino-3-nitro-4-quinolinecarboxamide, N-aryl-2-amino-3-nitro-4-quinolinecarboxamide, N-acyl-2-amino-3-nitro-4-quinolinecarboxamide, N,N-dialkyl-2-amino-3-nitro-4-quinolinecarboxamide, 2-amino-3-nitro-4-quinolinesulfonamide, N-alkyl-2-amino-3-nitro-4-quinolinesulfonamide, N-alkenyl-2-amino-3-nitro-4-quinolinesulfonamide, N-aryl-2-amino-3-nitro-4-quinolinesulfonamide, N-acyl-2-amino-3-nitro-4-quinolinesulfonamide, N,N-dialkyl-2-amino-3-nitro-4-quinolinesulfonamide, 2-amino-4-acetyl-3-nitroquinoline, 2-amino-4-alkenylcarbonyl-3-nitroquinoline, 2-amino-4-arylcarbonyl-3-nitroquinoline, 2-amino-4-benzylcarbonyl-3-nitroquinoline, 2-amino-4-alkoxycarbonyl-3-nitroquinoline, 2-amino-4-alkenyloxycarbonyl-3-nitroquinoline, 2-amino-4-(N-benzylamino)-3-nitroquinoline, N-benzyl-2-amino-3-nitro-4-quinolinesulfonamide, N-benzyl-2-amino-3-nitro-4-quinolinecarboxamide and isomers of the above 2-amino-4-substituted-3-nitroquinolines, the isomers having a substituent on the 2-position and an amino group on the 4-position, 3-amino-4-nitroquinoline, 3-amino-2-halogeno-4-nitroquinoline, 3-amino-2-cyano-4-nitroquinoline, 3-amino-2-aryl-4-nitroquinoline, 3-amino-2-alkyl-4-nitroquinoline, 3-amino-2-alkenyl-4-nitroquinoline, 3-amino-2-hydroxy-4-nitroquinoline, 3-amino-2-alkoxy-4-nitroquinoline, 3-amino-2-alkenyloxy-4-nitroquinoline, 3-amino-2-aryloxy-4-nitroquinoline, 3-amino-2-benzyloxy-4-nitroquinoline, 3-amino-2-acyloxy-4-nitroquinoline, 2,3-diamino-4-nitroquinoline, 3-amino-2-(N-alkylamino)-4-nitroquinoline, 3-amino-2-(N-alkenylamino)-4-nitroquinoline, 3-amino-2-(N-arylamino)-4-nitroquinoline, 3-amino-2-(N-benzylamino)-4-nitroquinoline, 3-amino-2-(N-acylamino)-4-nitroquinoline, 3-amino-2-(N,N-dialkylamino)-4-nitroquinoline, 3-amino-2,4- dinitroquinoline, 3-amino-2-benzyl-4-nitroquinoline, 3-amino-4- nitro-2-quinolinecarboxylic acid, 3-amino-2-aryloxycarbonyl-4-nitroquinoline, 3-amino-2-benzyloxycarbonyl-4-nitroquinoline, 3-amino-2-mercapto-4-nitroquinoline, 3-amino-2-alkylthio-4-nitroquinoline, 3-amino-2-alkenylthio-4-nitroquinoline, 3-amino-2-arylthio-4-nitroquinoline, 3-amino-2-benzylthio-4-nitroquinoline, 3-amino-2-acylthio-4-nitroquinoline, 3-amino-4-nitro-2-quinolinesulfonic acid, alkyl 3-amino-4-nitro-2-quinolinesulfonate, alkenyl 3-amino-4-nitro-2-quinolinesulfonate, aryl 3-amino-4-nitro-2-quinolinesulfonate, benzyl 3-amino-4-nitro-2-quinolinesulfonate, 3-amino-2-trifluoromethyl-4-nitroquinoline, 3-amino-2-chloromethyl-4-nitroquinoline, 3-amino-2-(2-methoxyethyl)-4-nitroquinoline, 3-amino-2-trifluoromethoxy-4-nitroquinoline, 3-amino-2-difluoromethoxy-4-nitroquinoline, 3-amino-2-(2-methoxyethoxy)-4-nitroquinoline, 3-amino-2-(2-chlorovinyl)-4-nitroquinoline, 3-amino-2-($\alpha$-styryl)-4-nitroquinoline, 3-amino-2-(3-methoxy-1-propenyl)-4-nitroquinoline, 3-amino-2-cycloalkyl-4-nitroquinoline, 3-amino-2-fluorocyclopropyl-4-nitroquinoline, 3-amino-2-(2-oxazolinyl)-4-nitroquinoline, 3-amino-2-(4-piperidyl)-4-nitroquinoline, 3-amino-2-alkylsulfonyl-4-nitroquinoline, 3-amino-2-alkenylsulfonyl-4-nitroquinoline, 3-amino-2-arylsulfonyl-4-nitroquinoline, 3-amino-2-benzylsulfonyl-4-nitroquinoline, 3-amino-4-nitro-2-quinolinecarboxamide, N-alkyl-3-amino-4-nitro-2-quinolinecarboxamide, N-alkenyl-3-amino-4-nitro-2-quinolinecarboxamide, N-aryl-3-amino-4-nitro-2-quinolinecarboxamide, N-acyl-3-amino-4-nitro-2-quinolinecarboxamide, N,N-dialkyl-3-amino-4-nitro-2-quinolinecarboxamide, 3-amino-4-nitro-2-quinolinesulfonamide, N-alkyl-3-amino-4-nitro-2-quinolinesulfonamide, N-alkenyl-3-amino-4-nitro-2-quinolinesulfonamide, N-aryl-3-amino-4-nitro-2-quinolinesulfonamide, N-acyl-3-amino-4-nitro-2-quinolinesulfonamide, N,N-dialkyl-3-amino-4-nitro-2-quinolinesulfonamide, 3-amino-2-acetyl-4-nitroquinoline, 3-amino-2-alkenylcarbonyl-4-nitroquinoline, 3-amino-2-arylcarbonyl-4-nitroquinoline, 3-amino-2-benzylcarbonyl-4-nitroquinoline, 3-amino-2-alkoxycarbonyl-4-nitroquinoline, 3-amino-2-alkenyloxycarbonyl-4-nitroquinoline, 3-amino-2-(N-benzylamino)-4-nitroquinoline, N-benzyl-3-amino-4-nitro-2-quinolinesulfonamide, N-benzyl-3-amino-4-nitro-2-quinolinecarboxamide, etc. Furthermore, compounds having a 5,6,7,8-tetrahydroquinoline ring, a 5,6,7,8-tetrahydro[1,6]naphthyridine ring, a 7,8-dihydro-5H-pyrano[4,3-b]pyridine ring or a 7,8-dihydro-5H-thiopyrano[4,3-b]pyridine ring instead of a quinoline ring of the above aminated quinoline derivatives are included.

In addition, compounds having a N-oxide unit instead of a nitrogen atom of 1-position in all the above aminated pyridine derivatives and aminated quinoline derivatives are also included.

Compounds of formula [2] can be made according to methods described in "The Chemistry of Heterocylclic Compounds, Pyridine and Its Derivatives", Part Two, Chapter VIII, p. 470 (Edited by Erwin Klingsberg, 1961, Interscience Publishers Inc., New York) and Ullmann'Encyclopedia of Industrial Chemistry Vol. A22, Pyridine and Pyridine Derivatives, p. 399 (Edited by Barbara Elvers et al. VCH Verlagsgessellschaft mbH D-69451, Weinheim, 1993), which are hereby incorporated by reference.

Examples of the O-substituted hydroxylamine represented by general formula [3] used in the present invention include O-methylhydroxylamine, O-ethylhydroxylamine, O-tert-butylhydroxylamine, N,O-dimethylhydroxylamine, O-benzylhydroxylamine, N-cyclohexyl-O-methylhydroxylamine, N-benzyl-O-methylhydroxylamine, etc. The O-substituted hydroxylamine may be used in the uncombined form or in the form of an inorganic salt such as a hydrochloride, a sulfate, etc.

As the metal catalyst in the present invention, for example, various transition metals such as copper, manganese, iron, nickel, cobalt, silver, chrome, zinc, etc. or compounds thereof can be used. Examples of such metal compounds include halides, oxides, sulfides, hydroxides, carboxylates, nitrates, sulfates, carbonates, phosphates, thiocyanates, chromates, perchlorates, alkoxides, cyanides, acetylacetonates, thiolates, amine complexes, pyridine complexes and pyridine N-oxide complexes of the above-listed metals.

As the metal catalyst, for example, there can be used copper, copper (I) chloride, copper (II) chloride, copper (I) bromide, copper (II) bromide, copper (I) iodide, copper (II) iodide, copper (I) oxide, copper (II) oxide, copper sulfide, copper acetate, copper nitrate, copper sulfate, copper carbonate, copper hydroxide, copper cyanide, copper acetylacetonate, copper phosphate, copper thiocyanate, copper chromate, copper perchlorate, copper methoxide, thiophenol copper, copper-pyridine complex, copper-pyridine N-oxide complex, zinc chloride, zinc fluoride, zinc iodide, zinc acetate, zinc naphthenate, zinc nitrate, zinc sulfate, zinc oxide, zinc sulfide, zinc thiocyanate, zinc pyrithione, zinc-pyridine complex, zinc-pyridine N-oxide complex, manganese chloride, cobalt chloride, nickel chloride, iron (II) chloride, iron (III) chloride, various iron oxides, silver oxide, etc. can be used. Among them, copper compounds and zinc compounds are preferred. The zinc compounds are particularly preferred. A halide, a carboxylate, a nitrate and a sulfate of zinc are especially preferred. In addition, these metal compounds containing crystal water can also be used.

The reaction is conducted in the presence of a base, but the base is not specifically limited. For example, there can be suitably used an alkali metal compound such as an alkali metal hydroxide, an alkali metal hydride, an alkali metal amide, an alkali metal alkoxide, etc. Examples of the base include sodium hydroxide, potassium hydroxide, sodium hydride, sodium amide, lithium amide, lithium diisopropylamide, sodium methoxide, sodium ethoxide, potassium tert-butoxide, etc.

The O-substituted hydroxylamine or a salt thereof is generally sued in the range of about 0.5 mol to about 5 mol, preferably in the range of about 0.8 mol to about 2 mol, per mol of the nitropyridines [2].

The metal catalyst is generally used in the range of about 0.1 mol to about 5 mol, preferably in the range of about 0.8 mol to about 1.2 mol, per mol of the nitropyridines [2]. The base is, in general, used in the range of about 1 mol to about 15 mol, preferably in the range of about 2 mol to about 5 mol, per mol of the nitropyridines [2].

In general, the reaction is conducted in the presence of a solvent. Examples of the solvent include an aprotic polar solvent such as N,N-dimethylformamide, dimethyl sulfoxide, 1,3-dimethyl-2-imidazolidinone, sulfolane, N-methyl-2-pyrrolidone, etc.; an ether solvent such as diethyl ether, ethylene glycol dimethyl ether, diethylene glycol dimethyl ether, triethylene glycol dimethyl ether, 1,4-dioxane, tetrahydrofuran, diethoxymethane, etc.; an aromatic solvent such as benzene, toluene, chlorobenzene, etc.;

an aromatic heterocyclic solvent such as pyridine, etc.; an aliphatic hydrocarbon solvent such as hexane, heptane, etc.; an alcohol solvent such as tert-butylalcohol, etc.; liquid ammonia, etc. These may be used alone or in combination.

The amount of the solvent to be used is in a range of about 1 to about 200 times by weight to the nitropyridines [2].

The reaction temperature is generally within the range of about −40° C. to about 100° C., preferably about 0° C. to about 50° C.

The objective compound produced by the process of the present invention can be easily isolated and purified from a reaction mixture, using conventional means such as distillation, extraction, recrystallization, various chromatographies, etc.

An aminonitropyridine of general formula [1] can be prepared by mixing and reacting a nitropyridine of general formula [2] with and O-substituted hydroxylamine or salt thereof in the presence of a base and a metal catalyst. Exemplary embodiments of a process of the present invention include that a mixture of a nitropyridine of general formula [2] and an O-substituted hydroxylamine or salt thereof is added to a mixture of a base and a metal catalyst.

According to the present invention, an aminonitropyridine which is useful as an intermediate in the production of drugs or agricultural chemicals can be produced quickly, cheaply and safely. Thus, the present invention provides an extremely useful industrial process. Processes for producing aminonitropyridines are also described in Japanese Application Nos. 07-069203 and 07-315234 which are hereby incorporated by reference.

EXAMPLES

The following Examples further illustrate the present invention in detail but are not to be construed to limit the scope thereof.

The following abbreviations are used in the Examples. DMF: N,N-dimethylformamide, DMSO: dimethyl sulfoxide, THF: tetrahydrofuran, DEM: diethoxymethane, DME: ethylene glycol dimethyl ether, Me: methyl group.

Example 1

6-Methoxy-3-nitropyridine (154 mg, 1 mmol) and O-methylhydroxylamine (71 mg, 1.5 mmol) were dissolved in DMSO (2 ml), and a resulting solution was added dropwise to a DMSO solution (3 ml) containing potassium tert-butoxide (336 mg, 3 mmol) and zinc (II) chloride (136 mg, 1 mmol) at 25° C. After completion of the addition, the resulting mixture was stirred at 25 ° C. for 9 hours and an aqueous saturated ammonium chloride solution (50 ml) was added, followed by extraction with ethyl acetate (80 ml). A resulting organic layer was dried over anhydrous magnesium sulfate, and then isolated and purified by subjection to silica gel thin layer chromatography [eluent: ethyl acetate/hexane=1/1] to obtain 147 mg of 2-amino-6-methoxy-3-nitropyridine (yield: 87%).

Examples 2 to 13

Aminonitropyridines were prepared according to the same manner as that described in Example 1 except for change 6-methoxy-3-nitropyridine and DMSO as shown in Table 1: Results are shown in Table 1.

TABLE 1

| Example No | $X_1$ | $X_2$ | $X_3$ | Solvent | Position to be aminated | Conversion rate (%) | Yield (%) |
|---|---|---|---|---|---|---|---|
| 2 | 6-MeO | H | H | DEM | 2 | 88 | 62 |
| 3 | 6-MeO | H | H | THF | 2 | 93 | 59 |
| 4 | 6-MeO | H | H | DME | 2 | 86 | 43 |
| 5 | 6-MeO | H | H | toluene | 2 | 78 | 19 |
| 6 | 2-Cl | H | H | DMSO | 4,6 | 97 | 36 (28/8) |
| 7 | 2-Cl | H | H | DME | 4 | 89 | 34 |
| 8 | 2-Cl | H | H | DEM | 4 | 54 | 24 |
| 9 | 6-Cl | H | H | DME | 2,4 | 82 | 22 (9/13) |
| 10[1] | 2-$NH_2$ | H | H | DMSO | 6 | 68 | 58 |
| 11[1] | 2-$NH_2$ | H | H | DMF | 6 | 100 | 53 |
| 12[1] | 6-$NH_2$ | H | H | DEM | 2 | 65 | 17 |
| 13[1] | 6-OH | H | H | DEM | 2 | 53 | 9 |

[1]Potassium tert-butoxide (4 mmol) was used.

Example 14

23 mg of 2,6-diamino-3-nitropyridine was obtained according to the same manner as that described in Example 1 except for using 2-amino-3-nitropyridine (139 mg, 1 mmol) in place of 6-methoxy-3-nitropyridine and using potassium hydroxide (4 mmol) in place of potassium tert-butoxide (yield: 15%).

Example 15

4-Nitropyridine (124 mg, 1 mmol) and O-methylhydroxylamine (71 mg, 1.5 mmol) were dissolved in DMF (2 ml), and a resulting solution was added dropwise to a DMF solution (3 ml) containing potassium tert-butoxide (336 mg, 3 mmol) and zinc (II) chloride (136 mg, 1 mmol) at 25° C. After completion of the addition, the resulting mixture was at 25° C. for one hour and an aqueous saturated ammonium chloride solution (50 ml) was added, followed by extraction with ethyl acetate (80 ml). A resulting organic layer was dried over anhydrous magnesium sulfate, and then isolated and purified by subjecting to silica gel thin layer chromatography (eluent: ethyl acetate/hexane=1/1] to obtain 35 mg of 3-amino-4-nitropyridine (yield: 25%).

Example 16

43 mg of 3-amino-4-nitropyridine was obtained according to the same manner as that described in Example 15 except for using zinc pyrithione (317 mg, 1 mmol) in place of zinc (II) chloride (yield: 31%).

Example 17

39 mg of 3-amino-4-nitropyridine was obtained according to the same manner as that described in Example 15 except for using zinc naphthenate (817 mg) in place of zinc (II) chloride (yield: 28%).

Example 18

43 mg of 3-amino-4-nitropyridine was obtained according to the same manner as that described in Example 15 except for using lithium amide (69 mg, 3 mmol in place of potassium tert-butoxide (yield: 31%).

Example 19

4-Nitropyridine N-oxide (140 mg, 1 mmol) and O-methylhydroxylamine (71 mg, 1.5 mmol) were dissolved in DMF (2 ml), and a resulting solution was added dropwise to a DMF solution (3 ml) containing potassium tert-butoxide (336 mg, 3 mmol) and zinc (II) chloride (136 mg, 1 mmol) at 25° C. After completion of the addition, the resulting mixture was stirred at 25° C. for one hour and an aqueous saturated ammonium chloride solution (50 ml) was added, followed by extraction with ethyl acetate (80 ml). A resulting organic layer was dried over anhydrous magnesium sulfate, and then isolated and purified by subjecting to silica gel thin layer chromatography [eluent: ethyl acetate] to obtain 58 mg of 3-amino-4-nitropyridine N-oxide (yield: 38%).

Example 20

54 mg of 3-amino-4-nitropyridine N-oxide was obtained according to the same manner as that described in Example 19 except for using copper (I) chloride (99 mg, 1 mmol) in place of zinc (II) chloride (yield: 35%).

Example 21

26 mg of 3-amino-4-nitropyridine N-oxide was obtained according to the same manner as that described in Example 19 except for using cobalt (II) chloride (130 mg, 1 mmol) in place of zinc (II) chloride (yield: 17%).

Example 22

43 mg of 3-amino-4-nitroquinoline N-oxide was obtained according to the same manner as that described in Example 19 except for using 4-nitroquinoline N-oxide (190 mg, 1 mmol) in place of 4-nitropyridine N-oxide (yield: 21%).

Examples 23 to 53

Aminonitropyridines (compounds [1] shown in Table 2) are prepared according to the same manner as that described in Example 1 except for changing 6-methoxy-3-nitropyridine to compounds [2] shown in Table 2.

TABLE 2

| Expl. No. | Compound [2] | | | | | Compound [3] | | Compound [1] | | | | | | |
|---|---|---|---|---|---|---|---|---|---|---|---|---|---|---|
| | $X^1$ | $X^2$ | $X^3$ | Y | $NO_2$-Position | $R^4$ | $R^5$ | $X^1$ | $X^2$ | $X^3$ | Y | $R^4$ | $NO_2$-Position | Position to be aminated |
| 23 | 2-MeO | H | H | — | 4 | H | Me | 2-MeO | H | H | — | H | 4 | 3,5 |
| 24 | 2-MeO | H | H | O | 4 | H | Me | 2-MeO | H | H | O | H | 4 | 3,5 |
| 25 | 2-Cl | H | H | — | 4 | H | Me | 2-Cl | H | H | — | H | 4 | 3,5 |
| 26 | 2-Cl | H | H | O | 4 | H | Me | 2-Cl | H | H | O | H | 4 | 3,5 |
| 27 | 3-MeO | H | H | — | 4 | H | Me | 3-MeO | H | H | — | H | 4 | 5 |
| 28 | 3-Cl | H | H | — | 4 | H | Me | 3-Cl | H | H | — | H | 4 | 5 |
| 29 | 2-MeO | 6-MeO | H | — | 4 | H | Me | 2-MeO | 6-MeO | H | — | H | 4 | 3 |
| 30 | 2-Cl | 6-Cl | H | — | 4 | H | Me | 2-Cl | 2-Cl | H | — | H | 4 | 3 |
| 31 | 2-Cl | 3-MeO | H | — | 4 | H | Me | 2-Cl | 3-MeO | H | — | H | 4 | 5 |
| 32 | 2-EtO | H | H | — | 4 | H | Me | 2-EtO | H | H | — | H | 4 | 3,5 |
| 33 | 2-CF$_3$O | H | H | — | 4 | H | Me | 3-CF$_3$O | H | H | — | H | 4 | 3,5 |
| 34 | 3-CF$_3$O | H | H | — | 4 | H | Me | 3-CF$_3$O | H | H | — | H | 4 | 5 |
| 35 | 2-EtO | H | H | — | 3 | H | Me | 2-EtO | H | H | — | H | 3 | 4 |
| 36 | 2-MeO | H | H | — | 3 | H | Me | 2-MeO | H | H | — | H | 3 | 4 |
| 37 | 2-MeO | 6-Cl | H | — | 3 | H | Me | 2-MeO | 6-Cl | H | — | H | 3 | 4 |
| 38 | 3-CN | H | H | — | 4 | H | Me | 3-CN | H | H | — | H | 4 | 5 |
| 39 | 3-CN | H | H | O | 4 | H | Me | 3-CN | H | H | O | H | 4 | 5 |
| 40 | 4-CN | H | H | — | 3 | H | Me | 4-CN | H | H | — | H | 3 | 2 |
| 41 | 2-MeS | H | H | — | 3 | H | Me | 2-MeS | H | H | — | H | 3 | 4 |
| 42 | 6-MeS | H | H | — | 3 | H | Me | 6-MeS | H | H | — | H | 3 | 2,4 |
| 43 | 2-PhS | H | H | — | 3 | H | Me | 2-PhS | H | H | — | H | 3 | 4 |
| 44 | MeO (fused ring) | | H | — | 4 | H | Me | MeO (fused ring) | | H | — | H | 4 | 3 |
| 45 | Cl (fused ring) | | H | — | 4 | H | Me | Cl (fused ring) | | H | — | H | 4 | 3 |
| 46 | OEt (fused ring) | | H | — | 4 | H | Me | OEt (fused ring) | | H | — | H | 4 | 3 |

TABLE 2-continued

| | Compound [2] | | | | | Compound [3] | | Compound [1] | | | | | | |
|---|---|---|---|---|---|---|---|---|---|---|---|---|---|---|
| Expl. No. | $X^1$ | $X^2$ | $X^3$ | Y | $NO_2$-Position | $R^4$ | $R^5$ | $X^1$ | $X^2$ | $X^3$ | Y | $R^4$ | $NO_2$-Position | Position to be aminated |
| 47 | (cyclohexenyl 6,5) | OEt | H | O | 4 | H | Me | (cyclohexenyl 6,5) | OEt | H | O | H | 4 | 3 |
| 48 | (cyclohexenyl 6,5) | | H | — | 3 | H | Me | (cyclohexenyl 6,5) | | H | — | H | 3 | 2,4 |
| 49 | (cyclohexenyl 6,5) | 2-Cl | | O | 4 | H | Me | (cyclohexenyl 6,5) | 2-Cl | | O | H | 4 | 3 |
| 50 | (cyclohexenyl 6,5) | 2-Cl | | — | 3 | H | Me | (cyclohexenyl 6,5) | 2-Cl | | — | H | 3 | 4 |
| 51 | (O—O dioxy ring 6,5) | | H | — | 4 | H | Me | (O—O dioxy ring 6,5) | | H | — | H | 4 | 3 |
| 52 | (O ring 6,5) | | H | — | 4 | H | Me | (O ring 6,5) | | H | — | H | 4 | 3 |
| 53 | (NH ring 6,5) | | H | — | 4 | H | Me | (NH ring 6,5) | | H | — | H | 4 | 3 |

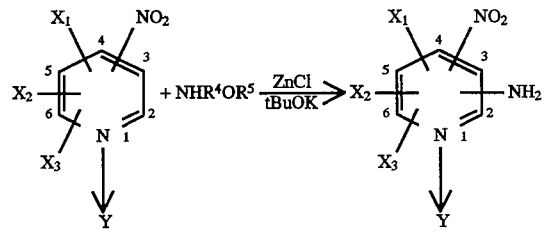

What is claimed is:

1. A process for producing an aminonitropyridine represented by the formula [1]:

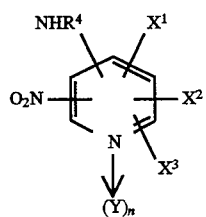

wherein $X^1$, $X^2$, $X^3$, $R^4$, Y and n are as defined below, which comprises reacting a nitropyridine represented by the formula [2]:

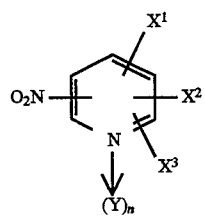

wherein $X^1$, $X^2$ and $X^3$ are the same or different and indicate a hydrogen atom, a halogen atom, a nitro group, a cyano group, an aryl group, a heterocycle, an alkyl group, a cycloalkyl group, an alkenyl group; said alkyl group, cycloalkyl group or alkenyl group being unsubstituted or substituted with a halogen atom, an aryl group, an amino group, a hydroxyl group, a carboxyl group or an alkoxyl group; or a group $OR^1$, $SR^1$, $NR^1R^2$, $COR^3$, $COOR^3$, $CONR^1R^2$, $SO_2R^3$, $SO_3R^3$ or $SO_2NR^1R^2$, or when two of $X^1$, $X^2$ and $X^3$ bond at the ortho-position, the two may bond together so that a 5- to 7-membered aromatic or nonaromatic hydrocarbon ring or heterocycle is formed which includes 2 carbon atoms of the pyridine ring; $R^1$ and $R^2$ are the same or different and indicate a hydrogen atom, an alkyl group, an alkenyl group; said alkyl group or alkenyl group being unsubstituted or substituted with a halogen atom, an aryl group, an amino group, a hydroxyl group, a carboxyl group or an alkoxyl group; an aryl group or an acyl group; $R^3$ is a hydrogen atom, an alkyl group, an alkenyl group; said alkyl group or alkenyl group being unsubstituted or substituted with a halogen atom, an aryl group, an amino group, a hydroxyl group, a carboxyl group or an alkoxyl group; or an aryl group; Y is an oxygen atom; and n is 0 or 1, with an O-substituted hydroxylamine represented by the formula [3]:

$$R^4NHOR^5 \qquad [3]$$

wherein $R^4$ is a hydrogen atom, an alkyl group, a cycloalkyl group or an aralkyl group; and $R^5$ is an alkyl group or an aralkyl group, or a salt thereof, in the presence of a base and a metal catalyst.

2. The process according to claim 1, wherein the O-substituted hydroxylamine represented by formula [3] or salt thereof is selected from the group consisting of an O-methylhydroxylamine, an O-ethylhydroxylamine, an O-tert-butylhydroxylamine, an O-benzylhydroxylamine, a N,O-dimethylhydroxylamine and salts thereof.

3. The process according to claim 1, wherein the salt of the O-substituted hydroxylamine represented by formula [3] is an inorganic acid salt.

4. The process according to claim 1, wherein the salt of the O-substituted hydroxylamine represented by formula [3] is a hydrochloride salt.

5. The process according to claim 1, wherein the base is an alkali metal compound.

6. The process according to claim 5, wherein the alkali metal compound is selected from the group consisting of an alkali metal alkoxide, an alkali metal hydroxide and an alkali metal amide.

7. The process according to claim 1, wherein the metal catalyst is selected from the group consisting of copper and copper compounds.

8. The process according to claim 7, wherein the copper compounds are a halide, a sulfide, a carboxylate, a nitrate, a sulfate, an acetylacetonate, an alkoxide, a hydroxide and a thiolate of copper.

9. The process according to claim 1, wherein the metal catalyst is selected from the group consisting of zinc and zinc compounds.

10. The process according to claim 9, wherein the zinc compounds are a halide, a sulfide, a carboxylate, a nitrate, a sulfate, an acetylacetonate, an alkoxide, a hydroxide and a thiolate of zinc.

11. The process according to claim 1, wherein the O-substituted hydroxylamine is used in the range of about 0.5 mol to about 5 mol per mol of the nitropyridine represented by formula [2].

12. The process according to claim 1, wherein the base is used in the range of about 1 mol to about 15 mol per mol of the nitropyridine represented by formula [2].

13. The process according to claim 1, wherein the metal catalyst is used in the range of about 0.1 mol to about 5 mol per mol of the nitropyridine represented by formula [2].

14. The process according to claim 1, wherein the reaction temperature is about −40° C. to about 100° C.

15. The process according to claim 1, wherein a mixture of the nitropyridine represented by formula [2] and the O-substituted hydroxylamine represented by formula [3] or salt thereof is added to a mixture of the base and the metal catalyst.

* * * * *